United States Patent [19]

Bommer et al.

[11] Patent Number: 4,656,186
[45] Date of Patent: Apr. 7, 1987

[54] TETRAPYRROLE THERAPEUTIC AGENTS
[75] Inventors: Jerry C. Bommer, Ogden; Bruce F. Burnham, Logan, both of Utah
[73] Assignee: Nippon Petrochemicals Co., Ltd., Tokyo, Japan
[21] Appl. No.: 728,785
[22] Filed: Apr. 30, 1985
[51] Int. Cl.[4] ..................... A61K 43/30; C07D 487/22
[52] U.S. Cl. .................................. 514/410; 514/322; 514/185; 540/145
[58] Field of Search .................... 260/112.5 R, 244.4, 260/245.91; 424/2; 514/2, 322, 410, 185

[56] References Cited

U.S. PATENT DOCUMENTS 4,393,071 7/1983 Fujii et al. ......................... 424/274

FOREIGN PATENT DOCUMENTS 2850676 3/1976 Japan .
84-01382 4/1984 PCT Int'l Appl. .

OTHER PUBLICATIONS

Tsvetkov et al., Chemical Abstracts, vol. 101 (1984) 110, 106a.
Fukuda et al., Chemical Abstracts, vol. 102 (1985) 122528y.
Cariello et al., Chemical Abstracts, vol. 90 (1979) 83836j.
Ballantine et al., Chemical Abstracts, vol. 93 (1980) 183058n.
Selve et al., Chemical Abstracts, vol. 95 (1981) 132845a.
Jackson et al., Chemical Abstracts, vol. 97 (1982) 144645q.
Chemical Berischet, 90, 470–481, 1957 by Lautsch et al.
Hoppe-Seyler's Ztschr. Phy Chem. 327, 205–216, 1962, Lossee and Muller.
Chimia, 13, 129–180, 1959, by Karrer.
Tetrahedron Letters, 23, 2017–2020, 1978, by Pelter et al.
Current Microbiology, 8, 195–199, 1983, by Gauthier et al.
Dougherty et al., Journal of the National Cancer Institute, 55, 1976, pp. 115–119.
Wile et al., "Laser Photoradiation Therapy of Recurrent Human Breast Cancer and Cancer of the Head and Neck," in Porphyrin Photosensitization, ed. by Kesser and Dougherty, Alan R. Liss, Inc., New York, NY, pp. 47–52 (1973).
Lin et al., "HpD Photodetection of Bladder Carcinoma," in Porphyrin Localization and Treatment of Tumors, ed. by Doiron and Gomer, Alan R. Liss, Inc. New York, NY, pp. 187–199 (1984).
Aizawa et al., "A New Diagnostic System for Malignant Tumors Using Hematoporphyrin Derivative, Laser Photoradiation and a Spectroscope," in Porphyrin Localization and Treatment of Tumors, ed. by Dorion and Gomer, Alan R. Liss, Inc., New York, NY, pp. 227–238 (1984).
Henderson et al., "Studies on the Mechanism of Tumor Destruction by Photoradiation Therapy," in Porphyrin Localization and Treatment of Tumors, ed. by Dorion and Gomer, Alan R. Liss, Inc., New York, NY, pp. 601–612 (1984).
Hayata et al., "Indications of Photoradiation Therapy in Early Stage Lung Cancer on the Basis of Post-PRT Histologic Findings," in Porphyrin Localization and Treatment of Tumors, ed. by Dorion and Gomer, Alan R. Liss, Inc., New York, NY, pp. 747–758 (1984).
Profio et al., "Fluorescence of Hematoporphyrin-Derivative for Detection and Characterization of Tumors, in Porphyrins in Tumor Photo-therapy, ed. by Andreoni and Cubeddu, Plenum Press, New York, NY, pp. 321–337 (1984).
Benson, Ralph C., "The Use of Hematoporphyrin Derivative (HpD) in the Localization and Treatment of Transition Cell Carcinoma (TCC) of the Bladder," in Porphyrin Localization and Treatment of Tumors, ed. by Dorion and Gomer, Alan R. Liss, Inc., New York, NY, pp. 795–804 (1984).
Fioretti et al., "Monitoring of Hematoporphyrin Injected in Humans and Clinical Prospects of Its Use in Gynecologic Oncology," in Porphyrins in Tumor Phototherapy, ed. by Andreoni and Cubeddu, Plenum Press, New York, NY, pp. 355–361 (1984).
Dorion et al., "Hematoporphyrin Derivative Photoradiation Therapy of Endobronchial Lung Cancer," in Porphyrins in Tumor Phototherapy, ed. by Andreoni and Cubeddu, Plenum Press, New York, NY, pp. 395–403 (1984).
Spinelli et al., "Endoscopic HpD-Laser Photoradiation Therapy (PRT) of Cancer," in Porphyrins in Tumor Phototherapy, ed. by Andreoni and Cubbeddu, Plenum Press, New York, NY, pp. 423–426 (1984).
Ohi et al., "Photoradiation Therapy with Hematoporphyrin Derivative and an Argon Dye Laser of Bladder Carcinoma," in Porphyrins in Tumor Phototherapy, ed. by Andreoni and Cubbeddu, Plenum Press, New York, NY, pp. 439–446 (1984).
Bruce, R. A., Jr., "Photoradiation for Chorodial Malignant Melanoma," in Porphyrins in Tumor Phototherapy, ed. by Andreoni and Cubbeddu, Plenum Press, New York, NY, pp. 455–461 (1984).
Berenbaum et al., "In Vivo Biological Activity of the Components of Haematoporphyrin Derivative," in Br. J. Cancer, 1982, pp. 571–581.

Primary Examiner—Richard L. Raymond
Attorney, Agent, or Firm—Scully, Scott, Murphy & Presser

[57] ABSTRACT

This invention relates to new fluorescent mono, di- or polyamide of an aminomonocarboxylic acid and a tetrapyrrole containing at least three carboxy groups of the structure:

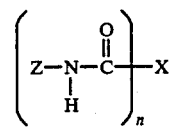

wherein Z is the amino acid residue and x is the tetrapyrrole residue and "n" is an integer from 1 to 4 inclusive.

14 Claims, No Drawings

TETRAPYRROLE THERAPEUTIC AGENTS

FIELD OF THE INVENTION

This invention relates to new compounds which are useful in photodiagnosis and phototherapy, especially in the detection and treatment of tumors and cancerous tissues in the human or animal body.

DESCRIPTION OF THE PRIOR ART

It is known to irradiate tumors and cancerous tissues in the human body with intensive light following administration of a hematoporphyrin derivative in the wavelength range of 626 to 636 namometers to reduce and, at times, destroy the cancerous cells (see PCT published specification WO 83/00811). It is also known that porphyrins, especially the sodium salt of protoporphyrins, can maintain or promote the normal functions of cells and are useful for preventing the genesis, growth, metastasis, and relapse of malignant tumors. Japanese Published Patent Application No. 125757/76 describes the use of porphyrins as tumor inhibiting agents, exemplifying etioporphyrin, mesoporphyrin, protoporphyrin, deuteroporphyrin, hematoporphyrin, coprophyrin, and uroporphyrin.

In Tetrahedron Letters No. 23, pp. 2017–2020 (1978), there is described an amino monocarboxylic acid adduct of the pigment bonellin obtained by extraction of principally the body wall of the marine echuroid *B. viridis*. The structure of these adducts is presumed to be an amide formed through either of the free carboxy groups of bonellin and the amino monocarboxylic acid. Hydrolysis of the adduct yielded a mixture of valine, isoleucine, leucine and alloisoleucine. No use for these amino acid adducts is described in this reference.

Mesoporphyrin and mesohaemin bis amino acid esters and the corresponding acids are described in *Chemische Berichte*, vol. 90, no. 4, 1957(pp. 470–481). Specific bis amino acid compounds include DL-valine, DL-leucine, DL-phenylalanine, DL-isoleucene and L-glutamic acid esters (and the corresponding free acids) bis-adducts of mesoporphyrin and mesohaemin. No therapeutic use of these compounds is disclosed, however.

PCT Patent Application No. WO 84/01382 describes the use of a new derivative of hematoporphyrin as useful in the localization and treatment of tumors.

That the tetrapyrroles cause intense photosensitivity in animals is well-known and has been documented in numerous articles in literature, e.g., J. Intr. Sci. Vitaminol, 27, 521-527 (1981); Agric. Biol. Chem., 46(9), 2183-2193 (1982); Chem. Abst. 98, 276 (1983) and 88, 69764m (1928).

SUMMARY OF THE INVENTION

The new products contemplated by this invention are aminomonocarboxylic acid adducts of tetrapyrroles containing at least three carboxylic acid groups. The present new compounds are mono-, di- or polyamides of an aminomonocarboxylic and a tetrapyrrole containing at least three carboxyl groups of the structure

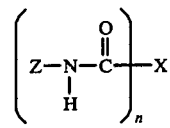

wherein Z is the aminomonocarboxylic acid residue less the amino group and X is the tetrapyrrole residue less the carboxy group and "n" is an integer from 1 to 4 inclusive.

The cyclic tetrapyrroles have as their common parent tetrapyrrole, uroporphyrinogen, and possess the following ring structure:

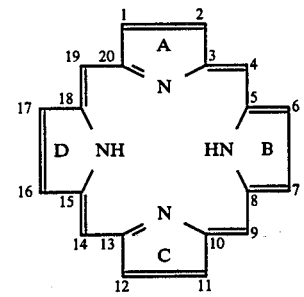

in which the positions in the molecule are numbered 1–20, and the rings identified by letters A, B, C and D, and also include perhydro-, e.g., dihydro- and tetrahydro-, derivatives of the said ring structure, e.g., compounds in which one or more double bonds are absent. There are present in the ring system four pyrrole rings joined through the alpha positions of the respective pyrrole rings by a methine group, i.e., —CH═. The compounds of the present invention are designated as derivatives of the tetrapyrroles for convenience in the disclosure and the appended claims and it will be understood that the term "tetrapyrrole" will designate compounds of the characteristic ring structure designated hereinbefore as well as the corresponding perhydro derivatives.

The tetrapyrroles employed in the present invention are all known or derived by various means and various alteration procedures from natural tetrapyrroles. The naturally occurring tetrapyrroles have as their common ancestor uroporphyrinogen III, a hexahydroporphydrin reduced at the bridge positions. The preferred tetrapyrrole carboxylic acids are those wherein at least three carboxylic acid groups are asymmetrically attached to the porphyrin ring system, e.g., the carboxylic acid groups are present on the rings A and B side of the molecule or on the rings D and C side of the molecule.

The particularly preferred tetrapyrrole compound of this invention are those represented by the formula:

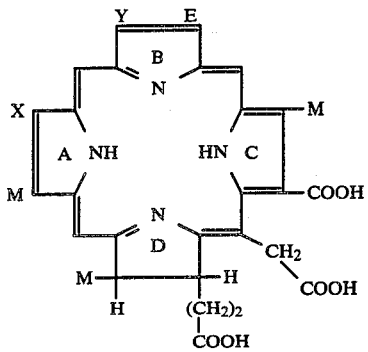

wherein;

X=H, vinyl, ethyl, acetyl or formyl;
Y=methyl or formyl;
M=methyl; and
E=ethyl and pharmaceutically-acceptable salts thereof.

A further characteristic of the present new compounds is the presence of at least one amide linkage in a substituent at any of the numbered positions of the ring structure. These are present in the instant new compounds together with other substituents as defined hereinafter.

Thus, the present invention contemplates amino acid or peptide derivatives of compounds which contain the chromophore of certain chlorins and bacteriochlorins, as well as related porphyrin compounds. The peptide linkage involves a carboxy group of the chromophore-bearing compound and the amino group of the specified amino acid. The present new compounds embrace derivatives of the tetrapyrroles which contain three carboxy groups. These derivatives include porphyrins of the major classes of tetrapyrroles: chlorins and bacteriochlorins, which are well-known to those skilled in this art.

The amino acid employed in the present invention to form the aforesaid peptide linkage are amino-monocarboxylic acids in which the amino group, of course, is located on a carbon atom of the carboxylic acid. The specific position of the amino group in the carbon atom chain is not critical, the only requirement being that the amino group be available to form the requisite peptide linkage with the carboxyl group of the selected porphyrin. Thus, a variety of amino monocarboxylic acids are useful in the present invention, including serine, glycine, methionine, α-alanine, β-alanine, α-phenylalanine, ε-aminocaproic acid, piperidine-2-carboxylic acid, pyrrole-2-carboxylic acid, piperidine-2-propionic acid, pyrrole-2-acetic acid, lysine, threonine, cysteine, and other natural amino acids. These amino acids may be substituted with angular alkyl groups such as methyl and ethyl groups, as well as other groups which do not adversely affect the capability of the amino group to form the peptide linkage, e.g., hydroxy, alkoxy groups or acyloxy groups, and may also include additional amino groups. The preferred amino acids are polar amino acids, particularly the naturally occurring polar α-amino acids, serine, methionine, threonine and cysteine, which are readily available and, up to the present, have provided the best results. For the purpose of this invention, "polar amino acids" include the amino acids containing, in addition to requisite amino and carboxylic acid groups, an oxygen, nitrogen or sulfur-containing groups, especially oxygen-containing groups such as hydroxy, acetoxy and methoxy groups.

Exemplary compounds of the tetrapyrrole classes are illustrated in Table I in which the numbered positions of the tetrapyrrole ring structure are used to designate the position of the indicated substituent. The absence of double bonds in the ring system is designated under "dihydro" with each set of numbers (ring position) indicating the absence of a double bond between the designated positions.

TABLE I

| | Ring Position | | | | | | | | | |
|---|---|---|---|---|---|---|---|---|---|---|
| | A | | B | | C | | D | | | |
| PORPHYRIN | 1 | 2 | 6 | 7 | 11 | 12 | 14 | 16 | 17 | Dihydro |
| Chlorin $e_6$ | Me | V | Me | Et | Me | $CO_2H$ | Ac | H | H | 16,17 |
| Mesochlorin $e_6$ | Me | Et | Me | Et | Me | $CO_2H$ | Ac | H | H | 16,17 |
| | | | | | | | | Pr | Me | |
| Bacteriochlorin $e_6$ | Me | ACL | H | H | Me | $CO_2H$ | Ac | H | H | 6,7 |
| | | | Me | Et | | | | Pr | Me | 16,17 |
| 2-Desvinylchlorin $e_6$ | Me | H | Me | Et | Me | $CO_2H$ | Ac | H | H | 16,17 |
| (or Deuterochlorin $e_6$) | | | | | | | | Pr | Me | |
| 2-Acetylchlorin $e_6$ | Me | ACL | Me | Et | Me | $CO_2H$ | Ac | H | H | 16,17 |
| | | | | | | | | Pr | Me | |
| 2-Formylchlorin $e_6$ | Me | CHO | Me | Et | Me | $CO_2H$ | Ac | H | H | 16,17 |
| | | | | | | | | Pr | Me | |
| Rhodin $g_7$ | Me | V | CHO | Et | Me | $CO_2H$ | Ac | H | H | 16,17 |
| | | | | | | | | Pr | Me | |

Notes:
Me: —$CH_3$ (Methyl group)
Pr: —$CH_2CH_2COOH$ (Propionic acid group)
V: —CH=$CH_2$ (Vinyl group)
Et: —$CH_2CH_3$ (Ethyl group)
Ac: —$CH_2COOH$ (Acetic acid group)
ACL: $CH_3$—OO— (Acetyl group)

Particularly preferred compounds of this invention include:

Chlorin Derivatives

Mono, di and triserinyl chlorin $e_6$
Mono, di and triserinyl mesochlorin $e_6$
Mono, di and trithreoninyl chlorin $e_6$
Mono, di and trithreoninyl chlorin $e_6$
Mono, di and triglycyl acetylchlorin $e_6$
Mono, di and triserinyl rhodin $g_7$
Mono, di and trimethionyl formylchlorin $e_6$
Mono, di and trithreoninyl rhodin $g_7$
Mono, di and tricysteinyl chlorin $e_6$
Mono, di and tricysteinyl rhodin $g_7$ Bacteriochlorine Derivatives
Mono, di and triserinyl bacteriochlorin $e_6$
Mono, di and trithreoninyl bacteriochlorin $e_6$
Mono, di and tricysteinyl bacteriochlorin $e_6$ The present new compounds form salts with either acids or bases. The acid salts are particularly useful for purification and/or separation of the final amide products as are the salts formed with bases. The base salts, however, are particularly preferred for diagnostic and therapeutic use as hereindescribed.

The acid salts are formed with a variety of acids such as the mineral acids, hydrochloric, hydrobromic, nitric and sulfuric acids, organic acids such as toluenesulfonic and benezenesulfonic acids.

The base salts include, for example, sodium, potassium, calcium, magnesium, ammonium, triethylammonium, trimethylammonium, morpholine and piperidine salts and similar such salts.

The acid and base salts are formed by the simple expediency of dissolving the selected amino acid tetrapyrrole amide in an aqueous solution of the acid or base and evaporation of the solution to dryness. The use of a water-miscible solvent for the amide can assist in dissolving the amide.

The final amide products can also be converted to metal complexes for example by reaction with metal salts. The magnesium complexes may be useful for the same purpose as the adduct product. Other metal complexes, as well as the magnesium complex, including, for example, iron and zinc, are useful to preclude contamination during processing of the adduct product by metals such as nickel, cobalt and copper, which are difficult to remove. Zinc and magnesium are readily removed from the final adduct product after processing is completed.

Since many of the aminodicarboxylic acids exist in both the D- and L-forms, and also are employed in mixtures of these forms as well as the D,L-form, the selection of the starting amino acid will, of course, result in products in which the respective isomer or mixture of isomers exist. The present invention contemplates the use of all such isomers, but the L-form is particularly preferred.

The present new compounds are prepared by the usual peptide synthetic routes which generally include any amide-forming reaction between the selected amino acid and the specific tetrapyrrole. Thus, any amide-forming derivative of the tetrapyrrole carboxylic acid can be employed in producing the present new peptides, e.g., lower alkyl esters, anhydrides and mixed anhydrides.

The preferred preparative methods use mixed anhydrides of the carboxylic acid or carbodiimides. The reactants are merely contacted in a suitable solvent therefor and allowed to react. Temperatures up to the reflux temperature can be used, with the higher temperatures merely reducing the reaction time. Excessively high temperatures are usually not preferred so as to avoid unwanted secondary reactions however.

The procedures for forming the instant peptides are well known in this art and are provided in detail in the accompanying examples.

When the selected tetrapyrrole contains at least three carboxyl groups, then mixtures of products can be formed including isomeric monopeptide products and di- and even tri- or higher peptide products, depending on the number of carboxyl groups and depending on the selected stoichiometry. Thus, when equimolar mixtures of amino acid and tetrapyrrole are reactd, not only monopeptides but also dipeptides are obtained, although the monopeptide would predominate. With higher molar ratios, the nature of the products will similarly vary. It is generally possible to separate the monopeptides and higher peptides using known chromatographic techniques. However, such separations are not necessary since the mixed peptides are usually comparable to the separated products in their ultimate use. Thus, mixtures of the mono-, di- and tripeptides of the same tetrapyrrole can be used.

Usually, unreacted tetrapyrrole is separated from the peptide products of the invention during purification as, for example, by chromatographic techniques.

Photodiagnosis and Phototherapy

The compounds of the present invention are useful for the photodiagnosis and phototherapy of tumor, cancer and malignant tissue (hereinafter referred to as "tumor").

When a man or animal having tumor is treated with doses of a compound of the present invention and when appropriate light rays or electromagnetic waves are applied, the compound emits light, i.e., fluorescence. Thereby the existence, position and size of tumor can be detected, i.e., photodiagnosis.

When the tumor is irradiated with light of proper wavelength and intensity, the compound is activated to exert a cell killing effect against the tumor. This is called "phototherapy".

Compounds intended for photodiagnosis and phototherapy ideally should have the following properties:

(a) non-toxic at normal therapeutic dosage unless and until activated by light;

(b) should be selectively photoactive;

(c) when light rays or electromagnetic waves are applied, they should emit characteristic and detectable fluorescence;

(d) when irradiated with light rays or electromagnetic waves are applied, they are activated to an extent to exert a cell killing effect against tumor; and (e) easily metabolized or excreted after treatment.

In accordance with testing up to the present, the present new compounds have the foregoing properties and are also characterized by reasonable solubility in saline at physiological pH.

The present new compounds possess greater fluorescence in tumors than do the corresponding basic tetrapyrroles. Their use provides the best contrast in tumors compared to normal tissue around the tumor. The instant compounds absorb activating energy for phototherapy in the convenient range of 600 to 800 nanometers, with the preferred compounds absorbing in the 620–760 nanometer range, i.e., light of longer wavelengths which more readily permits penetration of energy into the tumor for phototherapeutic purpose.

In presence experience, the present compounds more uniformly distribute throughout the tumor than the basic tetrapyrrole permitting the use of considerably lower dosage (to about 1/10th of the required normal dose of the basic tetrapyrrole) which lessens, if not eliminates, photosensitization in the host. They also possess a more consistent fluorescence whereas some of the corresponding tetrapyrroles show inconsistent fluorescence or the fluorescence varies from day to day in the host.

A particularly advantageous property of the present compounds resides in the ease with which they are excreted by the host. Generally, within 24 to 72 hours of intravenous or intraperitonal administration, there are little or no detectable amounts in normal muscle tissue. Up to about 50% of the present compounds are recovered from the feces of the host within 24–72 hours of injection whereas under equivalent circumstances, substantial amounts of the corresponding tetrapyrroles remain, and up to about 20% of peptides formed with amino monocarboxylic acids remain. This property is extremely important in that it contributes to minimization of photosensitization of the host.

The instant compounds can be used for diagnosis and therapeutic treatment of a broad range of tumors. Examples of tumors are gastric cancer, enteric cancer, lung cancer, breast cancer, uterine cancer, esophageal cancer, ovarian cancer, pancreatic cancer, pharyngeal cancer, sarcomas, hepatic cancer, cancer of the urinary bladder, cancer of the upper jaw, cancer of the bile duct, cancer of the tongue, cerebral tumor, skin cancer, malignant goiter, prostatic cancer, cancer of the parotid gland, Hodgkins's disease, multiple myeloma, renal cancer, leukemia, and malignant lymphocytoma. For diagnosis, the sole requirement is that the tumor be capable of selectively fluorescing when exposed to proper light. For treatment, the tumor must be penetrable by the activation energy. For diagnosis, light of shorter wavelength is used whereas for therapeutic purposes light of longer wavelength is used to permit ready penetration of the tumor tissue. Thus, for diagnosis, light of from 360–760 nanometers can be used, and for treatment, from 620 to 760, depending on the individual characteristics of the tetrapyrrole. The absorption characteristics of the present new compounds are substantially the same as the tetrapyrrole from which derived.

It is necessary that the light rays be so intense as to cause the compounds to emit fluorescence for diagnosis and to exert a cell killing effect for therapy.

The source of irradiation for photodiagnosis and phototherapy is not restricted, however, but the laser beam is preferable because intensive light rays in a desired wavelength range can be selectively applied. For example, in photodiagnosis, the compound of the invention is administered to a human or animal body, and after a certain period of time, light rays are applied to the part to be examined. When an endoscope can be used for the affected part, such as lungs, gullet, stomach, womb, urinary bladder or rectum, it is irradiated using the endoscope, and the tumor portion selectively emits fluorescence. This portion is observed visually, or observed through an adapted fiber scope by eye or on a CRT screen.

In phototherapy, after administration of the dosage, the irradiation is carried out by laser beams from the tip of quartz fibers. Besides the irradiation of the surface of tumor, the internal part of the tumor can be irradiated by inserting the tip of quartz fibers into the tumor. The irradiation can be visually observed or imaged on a CRT screen.

For photodiagnosis, light of wavelengths between 360 and 760 nm. is suitable for activating the present tetrapyrrole compounds. Of course, each compound has a specific optimal wavelength of activation. A long wavelength ultraviolet lamp is particularly suitable for photodiagnosis. Similar methods for viewing of the treated tumor can be used as already described for phototherapy.

The dosages of the present new compounds will vary depending on the desired effect, whether for diagnosis or for treatment. For diagnosis, doses of as little as 1 mg/kg will be effective, and up to about 7.5 mg/kg can be used. For treatment, the dose will usually approximate about 0.5 mg/kg. Of course, the dosage for either diagnosis or treatment can be varied widely in view of aforesaid advantageous properties of the present compounds, e.g., the ease of elimination from the host, for one.

The present compounds are apparently non-toxic at the dosage levels employed for diagnosis or treatment. No mortality of test animals due the present compounds has been noted in studies employing dosage levels up to 20 mg/kg.

For both diagnosis and treatment, the present compounds can be administered by the oral, intravenous, or intramuscular routes. They can be formulated as lyophilized sterile, pyrogen-free compounds, preferably in the form of basic salts, e.g., sodium salt. The preferred dosage forms are provided as injectable solutions (isotonic).

The irradiation source used in treatment of tumors containing compounds of this invention is a filtered, high-intensity, continuous source or pumped dye, or other laser and light delivery system, which is capable of performing within the following limits: power intensity 20–500 mw/cm$^2$ at wavelengths between 620 and 680 nm. and a total output of at least 4 watts or greater. Several currently commercially available lasers meet these criteria.

The tetrapyrroles can be prepared by various synthetic methods which are found in the literature, e.g., Chlorin e$_6$.

Willstatter, R., Stoll, A.; *Investigations on Chlorophyll*, (Trans., Schertz, F. M., Merz, A. R.,) p. 176. Science Printing Press, Lancaster, Pa., 1928.

Willstatter, R., Isler, M.; *Ann. Chem.*, 390, 269 (1912).

Fisher, H., Baumler, R.; *Ann. Chem.*, 474, 65 (1929).

Fisher, H., Siebel, H.; *Ann. Chem.*, 499, 84 (1932).

Conant, J. B., Mayer, W. W.; *J. Amer. Chem. Soc.*, 52, 3013 (1930).

Chlorin e$_6$, e$_4$, mesochlorin e$_6$, bacteriochlorin e$_6$

Fischer and Orth, "Des Chemie des Pyrrole" Akademische Verlazsgesellschaft, Leipzig, 1940, Vol. II, Part 2.

General Reference for Porphyrins

"Porphyrins and Metalloporphyrins" ed. Kevin M. Smith, Elsevier 1975 N.Y.

The compounds of the present invention can be administered to the host in a variety of forms adapted to the chosen route of administration, i.e., orally, intraveneously, intramuscularly or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, an addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporanous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The present new compounds may also be applied directly to tumors, whether internal or external, in the host in topical compositions. Exemplary compositions include solutions of the new compounds in solvents, particularly aqueous solvents, most preferably water. Alternatively, for topical application particularly to skin tumors, the present new compounds may be dispersed in the usual cream or salve formulations commonly used for this purpose or may be provided in the form of spray solutions or suspensions which may include a propellant usually employed in aerosol preparations.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatable with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of tumors in living subjects.

The following examples further illustrate the invention.

EXAMPLE 1

L-Monoserinyl chlorin $e_6$ (carbodiimide method)

150 mg of chlorin $e_6$ and 250 mg of L-serine t-butyl ester hydrochloride are dissolved in 20 ml of dimethyl formamide. There is made a total of 3-100 mg additions of N,N'-dicyclohexyl-carbodiimide at one hour intervals. After 4 hours, the reaction mixture is diluted with 300 ml ether, washed twice with 200 ml $H_2O$ then extracted with 40 ml 1M KOH. The KOH solution is allowed to hydrolyze overnight and then heated to 70° C. for 10 minutes.

The pH of the solution is adjusted to 7, and then any residual ether is removed by flash evaporation. The solution is then applied to a reverse phase (C-18 silica) column (1.5 cm×30 cm), and purified by a stepwise elution of methanol/0.01 m pH 6.85 $KPO_4$ buffer, eluted with 5% methanol until unwanted polar pigments were removed. Monoserinyl chlorin $e_6$ is eluted off with 6–8% methanol, and unreacted chlorin $e_6$ removed with 25% methanol.

The product is precipitated at pH 3 after flash evaporating briefly to remove methanol, and then washed at the centrifuge 3 times with dilute acetic acid.

The product is dried under vacuum.

EXAMPLE 2

L-Monocysteinyl chlorin $e_6$ (carbodiimide method)

130 mg of chlorin $e_6$ and 260 mg L-cysteine methyl ester hydrochloride are dissolved in 18 ml of dimethyl formamide. 100 mg of N,N'-dicyclohexylcarbodiimide is added and the reaction mixture stirred for 1 hour. 50 mg more carbodiimide is then added. After 1 hour, the reaction mixture appears to contain 75–80% of the monosubstituted product by reverse phase TLC (C-18 plates with 70% MeOH, 30% 0.01M $KPO_4$ pH 6.85). 200 ml Diethyl ether was added, washed twice with 100 ml $H_2O$, then extracted with 30 ml 1M KOH.

The product is allowed to hydrolyze in the dark in the KOH solution for 12 hours, then is heated to 70° C. for 10 minutes, to complete the hydrolysis of the ester groups. The product is then separated by reverse phase column chromatography (C-18 reverse phase silica 1.5 cm × 30 cm), using stepwise gradient elution with methanol in buffer 0.01M $KPO_4$ pH 6.85. 5% Methanol removed polar impurities. Chlorin $e_6$ is eluted off the column with 25% methanol. The methanol is removed by flash evaporation and the L-monocysteinyl chlorin $e_6$ is precipitated at pH 3, collected and washed 3 times at the centrifuge with dilute acetic acid, and dried under vacuum.

EXAMPLE 3

Mono and Di (L) Serinyl Chlorin $e_6$ (Carbodiimide Method)

400 mg of chlorin $e_6$ and 1 g of L-serine benzyl ester p-tosylate are dissolved in 75 ml of dimethylformamide. Temperature of the solution is maintained at 65°–70° C. with stirring and 100 mg of N,N'-dicyclohexyl carbodiimide is added. (A total of 3 additions are made at 2 hour intervals). The solution is allowed to stir at this temperature for a total of 20 hrs., then checked by TLC (reverse phase) (C-18 silica) plate, 70% methanol, 30% 0.01M pH 6.85 $KPO_4$ buffer. The TLC shows greater than 50% monosubstitution with some di-substitution.

150 ml of ether is added, and agitated with 100 ml of water and several drops of glacial acetic acid. The ether phase is separated and the aqueous phase extracted several more times with 100 ml of ether. The ether extracts are combined and washed with water (100 ml) four times to remove dimethylformamide.

The serinyl chlorin $e_6$ esters are then extracted into 100 ml of 1M KOH (4 extractions of 25 ml each). The KOH solution is allowed to stand at ambient temperature for 24 hours to hydrolyze. The components are separated by neutralizing the solution of pH 7 and applying to a reverse phase (C-18 silica) column (1.5 cm × 30 cm). The elution is performed using a 1 liter gradient of 30% mthanol to 80% methanol with 0.1M pH 6.85 $KPO_4$ buffer. Fractions are collected and characterized by TLC. The order of elution is di(L) diserinyl chlorin $e_6$, L-monoserinyl chlorin $e_6$ and chlorin $e_6$. Methanol is removed is flash evaporated and the individual components precipitated at pH 3, using HCl.

The products are collected by centrifugation, washed several times with very dilute acetic acid and dried under vacuum.

EXAMPLE 4

Di-(D,L) serinyl rhodin $g_7$ (Carbodiimide method)

140 mg of rhodin $g_7$ and 200 mg of (DL) serine methyl ester hydrochloride are dissolved in 30 ml of dimethyl formamide. 300 mg of N,N'-dicyclohexyl-carbodiimide is added. The reaction is allowed to stand for one hour, then another 300 mg of carbodiimide is added. This procedure is repeated twice and then the reaction mixture is allowed to stand overnight. The reaction may be monitored by thin layer chromatography on silica, using solvent benzene/methanol/88% formic acid 8.5/1.5/0.13 V/V/V.

The disubstituted rhodin $g_7$ has the the highest $R_f$ value, the unsubstituted rhodin $g_7$ has the lowest, with the monosubstituted isomers in between and unresolved.

After standing overnight, the reaction mixture appears to contain at least 50% of the disubstituted rhodin $g_7$. The solvent is removed under vacuum and the remaining solid dissolved in 50 ml of 3N HCl.

The solution is allowed to stand at room temperature for 48 hours to hydrolyze the ester groups, then the chlorin mixture is precipitated at pH 2.5–3 and collected and washed with water at the centrifuge.

The rhodin $g_7$ mixture is purified by dissolving in 0.05M $NH_4OH$ and applying to a reverse phase (C-18 silica) column 2.5 cm × 30 cm. The solution procedure is a linear gradient from 40 to 70% methanol in 0.01M $KPO_4$ buffer pH 6.85 (1 liter total volume).

The leading rhodin $g_7$ is collected and flash evaporated to remove the methyl alcohol, the solution then precipitated at pH 2.5–3 and collected and washed 3 times at the centrifuge with dilute acetic acid. The product is dried under vacuum.

EXAMPLE 5

Di and Mono (L) serinyl rhodin $g_7$ (mixed anhydride method)

50 mg (0.000087 moles) of rhodin $g_7$ is dissolved in 100 ml of tetrahydrofuran (THF). 0.210 l (0.002 moles) of triethylamine is added with stirring. After 10 minutes, 195 μl (0.00179 moles) of ethylchloroformate is added. After stirring 10 minutes, 50 ml (0.01 moles) of 0.2M KOH containing 250 mg (0.00169 moles) of (L) serine is added dropwise with stirring to the THF solution. This mixture is stirred 60 minutes at room temperature.

The organic solvent is flashed off and the reaction mixture is checked by silica TLC for product. Benzene/methanol/88% formic acid (8.5/1.5/0.13) is used to develop the chromatogram.

After checking for product, the solution is adjusted to pH 7.5–8.0 and placed on a reverse phase (C-18 silica) column 2.5 × 30 cm. The reaction mixture is resolved using a linear gradient of 40–80% methanol in 0.01M $KPO_4$ buffer pH 6.85 (1 liter total volume).

The column effluent is collected via fraction collector and the tube contents were pooled according to individual components. The order of elution is di(L)-serinyl rhodin $g_7$, mono (L) serinyl rhodin $g_7$ and unsubstituted rhodin $g_7$.

The methanol is flashed off and the material is precipitated at pH 2.5–3.0. The precipitate is washed 3 times with dilute acetic acid in water and the product dried under vacuum.

EXAMPLE 6

Mono Glycyl Chlorin $e_6$ (Mixed Anhydride Method)

625 mg of chlorin $e_6$ was dissolved in 300 ml of dimethyl formamide (DMF) and 277 μl (0.002 moles) of triethylamine (TEA) was added to the DMF solution. After stirring for five minutes, 201 μl (0.002 moles) of ethylchloroformate (EC) was added and stirred for 1½ hours at room temperature.

75 mg (0.0009 moles) of glycine (ammonia free) was added to the DMF solution and allowed to stir three hours at 50°-60° C.

The DMF solution was tested for product by reverse phase (C-18 silica) TLC using methanol/0.01M sodium phosphate buffer, pH 6.85, 70/30, to develop the chromatogram.

The DMF solution was flashed to near dryness, then dissolved in dilute NaOH and the pH adjusted to 2.5-3 to precipitate the solid. The precipitate was then placed on a reverse phase (C-18 silica) column 3.7 cm×45 cm.

Fractions were eluted, using 20-40% methanol in 0.01M sodium phosphate buffer, pH 6.85. The fractions were pooled according to individual components.

The methanol was flashed off and the material was precipitated at pH 2.5-3.0. The precipitate was washed and centrifuged 3 times in dilute acetic acid in water. The product was dried under vacuum. The yield of mono glycyl chlorin $e_6$ was 87.5 mg.

Utilizing the aforementioned carbodiimide or the mixed anhdyride methods, the following compounds of this invention can be synthesized:

(D,L)-Serinyl mesochlorin $e_6$
Glycyl chlorin $e_6$
Glycyl mesochlorin $e_6$
α-(D,L)-Alanyl chlorin $e_6$
α-(D,L)-Alanyl mesochlorin $e_6$
β-Alanyl chlorin $e_6$
β-Alanyl mesochlorin $e_6$
ε-Amino-n-caproyl chlorin $e_6$
ε-Amino-n-caproyl mesochlorin $e_6$
(D,L)-Serinyl bacteriochlorin $e_6$
Glycyl bacteriochlorin $e_6$
α-(D,L)-Alanyl bacteriochlorin $e_6$
β-Alanyl bacteriochlorin $e_6$
ε-Amino-n-caproyl bacteriochlorin $e_6$
Mono, di and triserinyl chlorin $e_6$
Mono, di and triserinyl mesochlorin $e_6$
Mono, di and trithreoninyl chlorin $e_6$
Mono, di and trithreoninyl mesochlorin $e_6$
Mono and diglycyl acetylchlorin $e_6$
Mono and diserinyl rhodin $g_7$
Mono and dimethionyl formylchlorin $e_6$
Mono and dithreoninyl rhodin $g_7$
Mono and dicysteinyl chlorin $e_6$
Mono, di and triserinyl bacteriochlorin $e_6$
Mono, di and trithreoninyl bacteriochlorin $e_6$
Mono, di and tricysteinyl bacteriochlorin $e_6$

EXAMPLE 7

Di-L-α-Serinyl chlorin $e_6$ (mixed anhydride method)

650 mg chlorin $e_6$ was dissolved in 30 ml of dimethylformamide (DMF). 277 μl (0.002 moles) of triethylamine was added to the DMF solution. After stirring for five minutes, 201 μl (0.002 moles) of ethyl chloroformate was added and stirring was continued for an additional 30 minutes. 0.95 g (0.009 moles) of L-α-serine was added to the DMF solution and allowed to stir for one hour at 50°-60° C.

The DMF solution was checked for product formation by reverse phase (C-18 silica) TLC using methanol/0.01M sodium phosphate buffer, pH 6.85, (7.0/3.0) to develop the choromatogram. The DMF solution was flash evaporated to near dryness and the reaction mixture was then taken up in dilute NaOH and the pH was adjusted to 2.5-3.0 to precipitate out the mixture. The precipitate was then centrifuged down and washed twice with diluted acetic acid in water. The precipitate was then centrifuged down and washed twice with diluted acetic acid in water. The precipitate was then redissolved in dilute NaOH and the pH adjusted to 7.0. This was applied to a reverse phase (C-18 silica) column 3.7 cm×45 cm.

The product was eluted from the column with a solution of 0.1M sodium phosphate buffer, pH 6.85/methanol (7.0/3.0). Fractions were collected and the fractions of pure di-L-α-serinyl chlorin $e_6$ were pooled. The methanol was flashed off and the product was precipitated at pH 2.5-3.0. The precipitate was centrifuged down and washed three times with dilute acetic acid in water. The product was lyophilized and produced a yield of 200 mg di-L-α-serinyl chlorin $e_6$.

Similarly, by utilizing other amino acids, peptides which further illustrate embodiments of, but do not limit the present invention, can be prepared using the procedure of Example 7:

Di, tri-(D,L)-serinyl chlorin $e_6$
Di, tri-(D,L)serinyl mesochlorin $e_6$
Di, tri-glycyl chlorin $e_6$
Di, tri-glycycl mesochlorin $e_6$
Di, tri-α-(D,L)-alanyl chlorin $e_6$
Di, tri-α-(D,L)-alanyl mesochlorin $e_6$
Di, tri-β-alanyl chlorin $e_6$
Di, tri-β-alanyl mesochlorin $e_6$
Di, tri-ε-amino-n-caproyl chlorin $e_6$
Di, tri-ε-amino-n-caproyl mesochlorin $e_6$
Di, tri-(D,L)-serinylbacteriochlorin $e_6$
Di, tri-glycylbacteriochlorin $e_6$
Di, tri-α-(D,L)-alanylbacteriochlorin $e_6$
Di, tri-β-alanylbacteriochlorin $e_6$
Di, tri-ε-amino-n-caproylbacteriochlorin $e_6$
Di, tri-histidyl chlorin $e_6$
Di, tri-histidyl mesochlorin $e_6$
Di, tri-arginyl chlorin $e_6$
Di, tri-arginyl mesochlorin $e_6$
Di, tri-tyrosyl chlorin $e_6$
Di, tri-tyrosyl mesochlorin $e_6$
Di, tri-methionyl chlorin $e_6$
Di, tri-methionyl mesochlorin $e_6$
Di, tri-cysteinyl chlorin $e_6$
Di, tri-cysteinyl mesochlorin $e_6$
Di, tri-threoninyl chlorin $e_6$
Di, tri-threoninyl mesochlorin $e_6$
Di, tri-leucyl chlorin $e_6$
Di, tri-leucyl mesochlorin $e_6$ Other amino acid derivatives of the tetrapyrroles can also be prepared. The following amino acids can also be used to prepare the di-, tri-, or where appropriate, the tetra-amino acid derivatives of the chlorins, porphyrins, or bacteriochlorins, employing the procedures of one of the aforementioned methods:

Piperidine-2-carboxylic acid;
Pyrrole-2-carboxylic acid;
Piperidine-2-propionic acid; and
Pyrrole-2-acetic acid.

Mixed amino acid derivatives of the tetrapyrroles can also be prepared. The various chlorin derivatives, porphyrin derivatives and bacteriochlorin derivatives can include any two or three of the following amino acids: Glycine, Serine, Threonine, Cysteine, Tyrosine, Asparagine, Glutamine, Lysine, Arginine, Histidine, α-Alanine, β-Alanine, Valine, Leucine, Isoleucine, Proline, α-Phenylalanine, β-Phenylalanine, Tryptophan, Methionine, ε-Amino-n-caproic acid, Piperidine-2-carboxylic acid, Pyrrole-2-carboxylic acid, Piperidine-2-propionic acid, Pyrrole-2-acetic acid.

The visible absorption spectrum in pyridine for all the amino acid derivatives of this invention are identical to that of the parent tetrapyrrole.

The following protocol describes the procedure for the use of the therapeutic compositions of the present invention in the treatment of rat tumors.

EXPERIMENTAL PROCEDURE

The photodynamic therapy experiments have been carried out on Buffalo rats, using the transplantable tumor, Morris Heptatoma 7777. The tumors were transplanted subcutaneously on the outside of the thigh. During treatment, the tumors ranges in size between 1 and 2.5 cm in diameter.

The general treatment regime is as follows. The rats are injected with a solution of the chlorin prepared as follows: 20 mg of the sodium salt of the chlorin was dissolved in 1 ml of 0.9% NaCl. The chlorin solution was then injected intravenously through the external jugular while the rat was anesthetized with ether. The volume of solution injected was calculated based upon the weight of the animal and the dosage, on a weight to weight basis, for the particular experiment. A specified time interval was then allowed to elapse before light treatment was instigated.

Light treatment of the rats was without anesthesia. The rats were restrained, the hair removed in the treatment area and treated with laser light from a Cooper Aurora argon pumped, tunable dye laser.

The laser was equipped with a fiber optic light delivery system coupled to a microlens system developed by Dr. Daniel Doiron, D. R. D. Consulting, Santa Barbara, Calif.

The lens disperses the laser beam, providing a circular distribution of light with homogenous light intensity throughout the area of the incident light beam. The wavelength of light was adjusted using a Hartridge reversion spectroscope. The light intensity was determined using a Yellow Springs Instrument, Model 65A, radiometer.

The micro lens was positioned at such a distance from the skin of the animal so as to provide an illumination diameter of 1.5 cm, and the light flux was varied by control of the laser output.

Subsequent to illumination, the animal was returned to its cage and, 24 hours later, it was treated intravenously in the external jugular vein with 14 mg of Evans Blue dye, dissolved in 250 μl of 0.9% NaCl. Two hours after injection, the rat was sacrificed and the tumor cross-sectioned. The extent of tumor necrosis was assessed by the lack of dye uptake[1], and the depth of the necrotic cross section of the tumor was recorded in millimeters.

(1) M. C. Berenbaum, Br. J. Cancer, 45: 571(1982)

Table III summarizes the effects of these drugs on tumors. The conditions described result in measurable and significant damage to the tumors.

In all cases except where noted, tissue damage occurred selectively to the tumor tissue as assayed by the Evans Blue method, even though, in nearly all cases, normal skin overlayed the tumor and the treatment area overlapped significant areas of normal muscle tissue.

The photodynamic therapy data is presented in tabular form. Column No. 2 is the total light dose administered in terms of Joules per square centimeter. Column No. 3 is the dose of chlorin administered in terms of mg of drug per kilogram of rat body weight. Column No. 4 is the time lapse between administration of drug and treatment with laser light. Column No. 5 is the wavelength of treatment light in nanometers. Column No. 6 is the intensity of the treatment light in milliwatts per square centimeter. In Column No. 7, $\bar{x}$ is the mean depth of necrosis in millimeters of the tumor tissue, i.e., the distance from the necrotic top of the tumor next to the skin to the necrotic edge of the tumor most distant from the skin.

S.D. is the standard deviation of $\bar{x}$.

(N) is the number of tumors or legs involved in the experiment.

Column No. 8 is the range of depth of necrosis in millimeters within the group.

TABLE III

| Tumor | Joules/cm$^2$ | Drug dose mg/kg | Time in hrs btwn drugs & light | Wave lnth nm | Intensity mW/cm$^2$ | $\bar{x}$ s.d. | (n) | Range mm |
|---|---|---|---|---|---|---|---|---|
| Mono Glycyl chlorin e$_6$ | | | | | | | | |
| 777 | 20 | 20 | 24 | 665 | 100 | 3.9 ± 3.0 | (5) | 2–9* |
| Mono-L-α-alanyl chlorin e$_6$ | | | | | | | | |
| 777 | 20 | 20 | 24 | 665 | 100 | 3.8 ± 1.8 | (2) | 2.5–5 |
| Mono-L-α-serinyl chlorin e$_6$ | | | | | | | | |
| 777 | 20 | 20 | 24 | 665 | 100 | 6.3 ± 2.7 | (6) | 3–10 |

1 of 8 tumors showed no necrosis due to drug and light.

What is claimed is:

1. A fluorescent mono, di or polyamide of an amino acid containing one carboxy group and a tetrapyrrole compound of the formula:

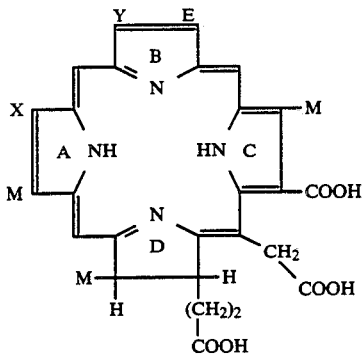

said amide being formed between the amino group of the amino acid and at least one of the carboxy moieties attached to said tetrapyrrole, wherein;

X = H, vinyl, ethyl, acetyl or formyl;
Y = methyl or formyl;
M = methyl; and
E = ethyl and pharmaceutically-acceptable salts thereof.

2. The amide according to claim 1 wherein the amino acid is an alpha amino acid.

3. The amide according to claim 1 wherein the amino acid is a polar alpha amino acid.

4. A mono- or diamide according to claim 1.

5. A mono- or diamide according to claim 1 wherein the amino acid is a polar amino acid.

6. Mono- or di-L-serinyl chlorin $e_6$.

7. Mono- or di-L-cysteinyl chlorin $e_6$.

8. Mono- or di-L-serinyl bacteriochlorin $e_6$.

9. Mono- or di-L-cysteinyl bacteriochlorin $e_6$.

10. Mono- or di-L-serinyl rhodin $g_7$.

11. Mono- or di-L-cysteinyl rhodin $g_7$.

12. Mono- or di-L-cysteinyl mesochlorin $e_6$.

13. Mono- or di-L-serinyl mesochlorin $e_6$.

14. A pharmaceutical composition comprising an effective therapeutic amount of a compound according to claim 1 and a pharmaceutical carrier therefor.

* * * * *